United States Patent [19]

Bolles et al.

[11] Patent Number: 4,834,989

[45] Date of Patent: May 30, 1989

[54] METHOD OF PRODUCING A HIGH FIBER FLAKED CEREAL

[75] Inventors: Albert D. Bolles, Marshall, Mich.; Joseph E. Spradlin, Monroe, N.Y.; Thomas L. Carpenter, Battle Creek, Mich.

[73] Assignee: General Foods Corporation, White Plains, N.Y.

[21] Appl. No.: 70,160

[22] Filed: Jul. 1, 1987

Related U.S. Application Data

[63] Continuation of Ser. No. 807,092, Dec. 10, 1985, abandoned.

[51] Int. Cl.$^4$ .................. A23L 1/105; A23L 1/164; A23L 1/20
[52] U.S. Cl. ........................ 426/28; 426/18; 426/44; 426/46; 426/52; 426/621; 426/648
[58] Field of Search .................. 426/18, 28, 52, 46, 426/618, 619, 620, 621, 560, 44, 648

[56] References Cited

U.S. PATENT DOCUMENTS

| | | | |
|---|---|---|---|
| 2,289,416 | 7/1942 | Fine et al. | 426/28 |
| 3,664,848 | 5/1972 | Bedenk et al. | 426/18 |
| 4,254,150 | 3/1981 | Fritze et al. | 426/18 |
| 4,350,714 | 9/1982 | Duvall | 426/621 |

*Primary Examiner*—Marianne Cintins
*Attorney, Agent, or Firm*—Sam D. Walker; Thomas R. Savoie; Daniel J. Donovan

[57] ABSTRACT

A process for preparing a crisp flaked cereal product having up to 8 grams of fiber per ounce of product comprising combining a starch degrading enzyme with a mixture of a farinaceous material and fiber and mixing the combination to form a uniform mixture followed by heating the uniform mixture to about 125° F. for about 3 minutes to activate the enzyme. The enzyme treated mixture is further cooked followed by drying to a moisture of about 18% then tempered for about 45 minutes followed by flaking and toasting to produce a cereal product with a moisture content of about 3%.

25 Claims, No Drawings

METHOD OF PRODUCING A HIGH FIBER FLAKED CEREAL

This application is a continuation of U.S. patent application Ser. No. 807,092 filed 12-10-85, now abandoned.

FIELD OF THE INVENTION

The present invention is concerned with a crisp fiber containing cereal. More particularly, the present invention is concerned with a high fiber flaked cereal product, said product having up to 8 grams of fiber per ounce of product.

BACKGROUND

Typically, fiber containing flaked cereals, such as bran flakes have been manufactured by combining a dried portion containing wheat and sufficient amounts of bran to produce a finished product having a fiber content of about 4 grams of fiber per ounce of cereal. These dry components are combined with a liquid portion made up mainly of flavor syrups. The combined portions are mixed and cooked until grits are formed. The grits are then dried, tempered, flaked and toasted to produce a finished product having a flake thickness of about 0.005 to 0.040 inches.

Attempts were made to increase the fiber content of flaked cereals to about 8 grams of fiber per ounce of cereal by increasing the amount of the bran component in the dried portion. However, any increase in bran component caused a significant decrease in flake size and most importantly caused a decrease in flake crispness. It is believed that an increase in fiber content of a flaked cereal dilutes the starch fraction of the flour causing a decrease in the ability of the component to agglomerate. Also, fiber preferentially absorbs moisture which decreases flake crispness. This explains why commercially available high fiber cereals are extruded and normally exhibit limited crispness.

It is known to treat cereal grain with enzymes during processing to aid in the breakdown of starches. For instance, U.S. Pat. No. 4,435,430 by Fulger et al. discloses an all-natural bran product made using enzymatic hydrolysis of the starch containing endosperm of a whole cereal grain. The process involves milling and separating a whole cereal grain; milling the bran fraction to a 5-100 microns particle size; hydrolyzing a slurry of the endosperm fraction with an enzyme, then recombining both fractions to form a cereal dough. This dough can then be formed into ready-to-eat cereal by any conventional method.

U.S. Pat. No. 4,431,674 by Fulger et al. discloses a ready-to-eat cereal prepared by a process almost identical to that described in U.S. Pat. No. 4,435,430 above. The difference being that the bran fraction in '674 is extruded under high temperature and pressure conditions in a counter-rotating twin screw extruder, instead of being milled as above. As in the above patent any whole grain, such as: corn, wheat, oats, barley, etc., may be employed.

U.S. Pat. No. 3,664,848 by Bedenk et al. discloses the production of high-protein, soy-containing breakfast cereal made from enzyme-hydrolyzed cereal grain of corn, wheat, rice and oats. The soy protein and a proteolytic enzymes are blended with a gelatinized cereal grain under high-pressure and temperature. The resulting product is pelletized and puffed to form a ready-to-eat breakfast cereal.

Other references such as U.S. Pat. No. 4,282,319 by Conrad discloses the use of enzyme in preparing ready-to-eat cereal product. Conrad discloses the use of hydrolyzing enzymes to degrade starch, while U.S. Pat. No. 4,217,414 by Walon discloses the addition of alpha-amylase to stabilize the starch fraction of a mixture of wheat gluten and wheat starch. Also, U.S. Pat. No. 4,254,150 by Fritze et al., U.S. Pat. No. 2,853,388 by Kiely et al. and U.S. Pat. No. 2,555,235 by Huzenlaub et al. disclose the treatment of cereal grain with enzymes or the degredation of the starch in cereal grain with enzymes.

None of the above-references, however, discloses the use of enzymes to produce a high-fiber, crisp, flaked cereal product.

It is, therefore, an object of the present invention to produce a high-fiber, flaked cereal product.

Another object of the present invention is to produce a flaked cereal product having up to 8 grams of fiber per ounce of cereal product.

A further object of the present invention is to produce a high-fiber, flaked cereal product that maintains its crispness in liquid for an extended period of time.

These and other objects will become more apparent from the following description of the invention.

SUMMARY OF THE INVENTION

The present invention is concerned with a process for preparing a crisp flaked cereal product comprising contacting a mixture comprising a farinaceous material having a flour content of 20 to 30%, and a fiber with a starch degrading enzyme wherein said mixture of farinaceous material and fiber are in amounts sufficient to form a finished product having up to 8 grams of fiber per ounce of cereal and said enzyme having sufficient enzyme activity to partially digest the starch fraction of the farinaceous material and fiber mixture; heating the enzyme treated mixture for a time and at a temperature effective to effect partial starch hydrolysis; heating the enzyme treated mixture further, for a time and at a temperature effective to deactivate the starch degrading enzyme and complete the starch gelatinization process to form agglomerates having a moisture ranging from 27% to 32%; drying the agglomerates for a time and at a temperature effective to form grits having a moisture ranging from 15% to 22%; tempering the grits for from 10 minutes to 180 minutes; flaking the grits; and toasting the grits for a time and at a temperature effective to produce a cereal product for packaging said product having a moisture ranging from 1.5 to 6.5%.

DETAILED DESCRIPTION

The present invention is concerned with the production of high fiber flaked cereal, said flake having up to 8 grams of fiber per ounce of product while maintaining its flake size and crispness in liquid for an extended period of time.

The first step of the present invention involves combining sufficient amounts of a farinaceous material and fiber to produce a finished product having up to 8 grams of fiber per ounce of product.

By "farinaceous material" is meant, a grain material (e.g., wheat, rice, oat, corn, peanut, etc.), grits, full fat, partially or wholly defatted grains, refined fraction of grain-like gluten and starches. Lesser optional fractions of non-grain materials (e.g., whole or ground seeds, like sesame seeds), beans, (e.g., whole defatted soy) and seeds (e.g., sun flower) are also considered farinaceous materials according to the present invention. The invention, however, will be described in terms of whole cracked wheat but is not intended to be limited thereto.

By "fiber" is meant the sum of insoluble and soluble polysaccharides resistant to digestion by alimentary enzymes. Sources of fiber include wheat bran, corn bran, oat bran, rice bran, soy bran and barley bran, but are not limited thereto.

The whole cracked wheat used in the present invention should have a flour content ranging from 20 to 30% and preferably about 25%. The amount of whole cracked wheat present in the farinaceous material fiber blend is dependent upon the desired fiber content in the finished product. The amount of whole cracked wheat in the blend should generally range from 40 to 70% of the blend and preferably about 55 to 60% of the blend.

The preferred source of fiber is wheat bran. The wheat bran may be of a red or white variety depending upon the desired fiber content. Typically, wheat bran has a fiber content ranging from 35 to 45%. The wheat bran used in the present invention is a combination of the red and white variety, the difference being the fiber and starch content, with the white variety having a higher starch and lower fiber content while the red variety has a lower starch and higher fiber content. Though 100% of each variety may be suitable, it is preferred, however, to utilize a blend of red and white wheat bran at a ratio of 55:45.

The whole cracked wheat is combined with the wheat bran at a ratio ranging from 99:1 cracked wheat to bran to 30:70. Preferably, the ratio of cracked wheat to bran should be at levels sufficient to produce a finished product having a fiber content of up to 8 grams of fiber per ounce of finished product. More preferable, the ratio of cracked wheat to bran should be 55:45 to 60:40 cracked wheat to bran. The flour content of the cracked wheat which will affect subsequent processing should be at levels ranging from 20 to 30% and preferably about 25%.

The method used to determine the fiber content in the present invention is the well-known Enzymatic-Gravimetric Method. A complete technical description of the methodology can be found in a publication entitled "Changes in Official Methods of Analysis," Journal of the Association of Official Analytical Chemist, Inc., Vol. 68, No. 2, page 399, 1985.

The blend of cracked wheat and bran is then contacted with a starch degrading enzyme. The starch degrading enzyme may be contacted to the cracked wheat bran mixture in a variety of ways, such as, spraying in solution and direct addition. It is preferred, however, to disperse the enzyme in an aqueous medium such as a flavor syrup, then contacting same to the dry blend.

The starch degrading enzyme is alpha amylase, one which is active within the pH range of from about 4.5 to 7.0 and which possesses appreciable activity at relatively low temperature, i.e., 100° to 150° F. Preferred sources of such alpha amylase include certain species of the bacteria microorganism, viz., *B. subtilis, B. licheniformis, B. coagulaus* and *B. amyloliquefaciens;* fungal microorganism viz., *Aspergillus niger, A. awamori,* and *A. oryzae;* plants viz., wheat, barley and sorghum; and mammalian viz., salivary gland and pancreas. The preferred alpha-amylase is that which is derived from *B. subtilis* strain, BAN 120 L, available from NOVO Enzyme Corporation, Wilton, Conn.

The activity of alpha-amylase must be sufficient to partially digest the starch present in the farinaceous material and fiber mixture. The enzyme activity should generally range from 10 to 40 units per gram of product and preferably about 25. One unit of amylase activity is the amount of enzyme that breaks down 5.26 grams of soluble starch per hour under standard conditions at a temperature of 37° C. and pH 5.6.

It is important in the present invention that there be limited or partial digestion of the starch. Therefore, the amount of alpha-amylase, its activity and exposure time to the starch in the product, plays an important function in the quality of the final product. An excess amount of the enzyme will accelerate the digestion process thereby destroying the crispness and ultimately the integrity of the final flakes. Too little alpha-amylase will result in a final product which absorbs moisture at too fast a rate resulting in rapid loss of crispness. The amount of alpha-amylase contacted with the farinacious/fiber blend should generally range from 0.01% to 0.03% by weight of the blend and preferably about 0.02% by weight. The alpha-amylase added is believed to modify the surface of the starch granule when processed into a cereal flake and alters its behavior towards moisture.

Endogenous sources of alpha-amylase may also be utilized in the present invention. For instance, whole grain such as whole wheat, corn, sorghum and the like, may be combined with water and steeped for a period of time ranging from 3 to 20 hours at a temperature ranging from 20° to 80° C. Steeping under these conditions initiates the germination reaction. This reaction initiates endogenous enzyme activity primarily alpha-amylase and beta-amylase which can be used to hydrolyze the starch fraction of the grain. It is also possible to utilize malted grains as an enzyme source, such as, malted wheat, malted sorghum, malted barley and the like. The enzymes produced above hydrolyze the starches to produce dextrins of various molecular weight which could be utilized in cereal processing for crispness phenomenon.

Other starch degrading enzyme such as pullulanase and iso-amylase may also be utilized in the present invention.

The combination of cracked wheat, bran and enzyme are mixed thoroughly and heated to a temperature ranging from 115° F. to 130° F. Lower temperatures prolong the time and should be avoided, while temperatures above 130° F. excessively gelatinizes the starch. The above time temperature conditions are designed to achieve the desired degree of enzyme activity and should be controlled sufficiently in order to avoid excessive digestion of the starch. The time necessary will be dependent upon various factors, such as, amount of starch to be digested, amount and type of alpha-amylase employed and temperature. A time period of greater than 4 minutes should be avoided because it causes excessive hydrolysis of the starch which affects the quality of the finished product. However, processing times ranging between about 2 and 4 minutes are acceptable with the preferred time being about 3.0 minutes.

The above heating step is controlled so that limited digestion of the starch occurs. The degree of digestion is affected by the time, temperature and moisture, since enzymes are protein in nature and are denatured or deactivated by heat. The enzyme activity is controlled so that after the above time temperature conditions are achieved the desired degree of digestion is accomplished. The temperature is maintained at the low end of the gelatinization curve thereby causing partial or mild gelatinization of the starch. It is believed that these conditions are necessary for the formation of certain dextrins which are essential in production of an acceptable finished product.

The partially digested mixture is further cooked for at time and at a temperature effective to form agglomerates. During cooking the mixture is agitated to ensure uniformity in heat distribution. The cooking temperature should generally range from 250° F. to 400° F. However, a temperature of about 300° F. is preferred. The cooking time is generally dependent upon the temperature within the cooker. For instance, as the temperature is increased the cooking time is decreased and vice versa. Generally, cooking times ranging from 20 to 60 minutes is suitable. However, the preferred cooking time should be about 35 minutes.

The moisture of the agglomerates exiting the cooker should generally range from 27 to 32% and preferably about 30% by weight.

The agglomerates are then transferred to a dryer an the moisture lowered to 15 to 22%. Drying may be done by any convenient means, such as by infra-red lamps, circulating air at room temperature or at elevated temperature, oven, etc. The drying process, of course, may be speeded up by spreading the grits on an extended surface, such as in shallow pans or on a conveyer belt, etc. If elevated temperatures are employed, it has been found preferable to maintain them at not over about 250° F. The preferred dryer is a rotary dryer. When a rotary dryer is utilized the temperature within the dryer should range from 200° F. to 300° F. and the time required to lower the agglomerates to the desired moisture conditions should range from 10 to 30 minutes. The dried product is referred to as grits.

After drying, the grits are then tempered. During tempering, the grits are allowed to cool down and equilibrate the moisture contained therein. This tempering has the effect of reducing the tackiness often times associated with partially processed cereal dough. A hold time ranging from 10 to 180 minutes is sufficient to temper the grits. However, it is preferred to temper the grits for 30 to 60 minutes.

The next step after tempering is flaking of the grits. This can be accomplished by passing the pellets between a pair of counter-rotating rollers or a roller and a flat surface spaced apart a distance sufficient to produce the desired flake thickness. In accordance with the present invention it is found that flake thickness of 0.005 to 0.040 inch is sufficient to produce a satisfactory product.

The mild enzymatic treatment enhances flake crispness when the fiber level of the product remains constant. This treatment also produces flakes of cereal with comparable crispness when the fiber content is up to 8 grams per ounce. When the fiber level was increased without enzymatic treatment, the grits produced were too small resulting in a significant reduction in flake size. Also, the finished product had a soft texture rather than the crisp texture of a conventional bran flake cereal. It is believed that the addition of the enzyme partially hydrolyze the starch fraction to form dextrins which affect flake size and water absorbent characteristics.

Additional processing steps can be utilized if it is so desired. For instance, a toasting operation may be employed after flaking if a rich golden brown color is desired. The toasting step also brings out a pleasant toasted fresh note. The moisture of the toasted product should range from 1.5 to 6.5% and preferably from 2.0 to 4.0%.

The present invention is further illustrated, but not limited by the following examples.

EXAMPLE I

A flaked cereal having 6 grams of fiber per ounce of product was prepared by first preparing a blend of dry ingredients made up of wheat bran in amounts of 43% by weight and cracked wheat in amounts of 57% (flour content 24.25).

The dry ingredients were then combined with a flavor syrup made by mixing malt syrup, water and 0.04% alpha-amylase.

The ratio of dry ingredients to flavor syrup was 65 to 35. The mixture of dry ingredients and syrup was uniformly blended and subsequently heated to 120° F. for 3 minutes. The mixture was further cooked for 30 minutes at 300° F. to form agglomerates. The moisture of the agglomerates after cooking was 30%.

The cooked agglomerates were then dried in a conventional rotary dryer for 25 minutes at a dryer temperature of 250° F. to form grits. The moisture of grits after drying was about 19%. The dried grits were then tempered by allowing to equilibrate for about 45 minutes. The tempered grits were flaked followed by toasting in an oven at 260° F. for 3 minutes. The toasted product had a moisture of 3%.

The finished product was crisp and crunchy and had flake thickness of about 0.02 inches typical of flaked bran cereal. The flake was then packaged for distribution.

What is claimed is:

1. A process for preparing a crisp flaked cereal product comprising:
   (a) contacting a mixture comprising a farinaceous material having a flour content of from 20 to 30% and a fiber with a starch degrading enzyme wherein said mixture of farinaceous material and fiber are in amounts sufficient to form a finished product having from 3.46 grams to 8 grams of fiber per ounce of cereal and said enzyme having sufficient enzyme activity to partially digest the starch fraction of the farinaceous material and fiber mixture;
   (b) heating the enzyme treated mixture for a time ranging from 2.0 to 4.0 minutes and at a temperature ranging from 115° F. to 130° F. to effect partial starch hydrolysis and starch gelatinization;
   (c) heating the enzyme treated mixture further for a time and at a temperature effective to deactivate the starch degrading enzyme and complete the starch gelatinization process to form agglomerates having a moisture ranging from 27 to 32%;
   (d) drying the agglomerates for a time and at a temperature effective to form grits having a moisture ranging from 15 to 22%;
   (e) tempering the grits for from 10 to 180 minutes;
   (f) flaking the grits; and
   (g) toasting the grits for a time and at a temperature effective to produce the cereal product for packaging said product having a moisture ranging from 1.5 to 6.5%.

2. A process according to claim 1 wherein the farinaceous material is a member selected from a group consisting of whole cracked wheat, corn, oat, barley, rice, rye, soy and combinations thereof.

3. A process according to claim 2 wherein the farinaceous material is whole cracked wheat.

4. A process according to claim 1 wherein the fiber is a member selected from a group consisting of wheat bran, corn bran, oat bran, rice bran, soy bran, barley bran and combinations thereof.

5. A process according to claim 4 wherein the fiber is wheat bran.

6. A process according to claim 1 wherein the ratio of farinaceous material to fiber ranges from 99:1 to 30:70.

7. A process according to claim 6 wherein the ratio of farinaceous material to fiber range from 55:45 to 60:40.

8. A process according to claim 1 wherein the starch degrading enzyme is a member selected from a group consisting of alpha-amylase, pullulanase, isoamylase, and combinations thereof.

9. A process according to claim 8 wherein the starch degrading enzyme is alpha-amylase.

10. A process according to claim 1(b) wherein the amounts of starch degrading enzyme ranges from 0.01% to 0.03% by weight.

11. A process according to claim 10 wherein the amounts of starch degrading enzyme is about 0.02% by weight.

12. A process according to claim 1 wherein the enzyme activity ranges from 10 to 40 units per gram of product of the blend.

13. A process according to claim 12 wherein the enzyme activity is about 25 units per gram of product.

14. A process according to claim 1 wherein the mixture of farinaceous material, fiber and enzyme are heated at a temperature of about 120° F.

15. A process according to claim 1 wherein the mixture of farinaceous material, fiber and enzyme are heated for a time of about 3 minutes.

16. A process according to claim 1 wherein the enzyme treated mixture is further cooked at a temperature ranging from 250° F. to 400° F.

17. A process according to claim 16 wherein the enzyme treated mixture is further cooked at a temperature of about 300° F.

18. A process according to claim 1 wherein the enzyme treated mixture is further cooked for a time ranging from 20 to 60 minutes.

19. A process according to claim 18 wherein the enzyme treated mixture is further cooked for a time of about 30 minutes.

20. A process according to claim 1 wherein the moisture of the agglomerates is about 30% by weight.

21. A process according to claim 1 wherein the agglomerates are dried at a temperature ranging from 200° to 300° F.

22. A process according to claim 1 wherein the agglomerates are dried for a time ranging from 10 to 30 minutes.

23. A process according to claim 1 wherein the agglomerates are dried for a time of about 18 minutes.

24. A process according to claim 1 wherein the grits are tempered for a time ranging from 30 to 60 minutes.

25. A process according to claim 1 wherein the flakes are toasted to a finished product moisture ranging from 2 to 4%.

* * * * *